(12) United States Patent
Wu et al.

(10) Patent No.: US 8,132,447 B2
(45) Date of Patent: Mar. 13, 2012

(54) UNIVERSAL TESTING MACHINE

(76) Inventors: Shaoming Wu, Thousand Oaks, CA (US); Richard Wu, Thousand Oaks, CA (US)

( * ) Notice: Subject to any disclaimer, the term of this patent is extended or adjusted under 35 U.S.C. 154(b) by 152 days.

(21) Appl. No.: 12/798,713

(22) Filed: Apr. 9, 2010

(65) Prior Publication Data
US 2011/0132078 A1 Jun. 9, 2011

Related U.S. Application Data

(60) Provisional application No. 61/283,902, filed on Dec. 9, 2009.

(51) Int. Cl.
*G01N 3/48* (2006.01)
*G01N 3/42* (2006.01)
*G01N 3/00* (2006.01)

(52) U.S. Cl. ............................................. 73/81; 73/796
(58) Field of Classification Search ................ 73/81, 82, 73/796
See application file for complete search history.

(56) References Cited

U.S. PATENT DOCUMENTS

| | | | |
|---|---|---|---|
| 5,305,633 A * | 4/1994 | Weissenbacher et al. | 73/82 |
| 6,279,388 B1 * | 8/2001 | Tsujii et al. | 73/82 |
| 7,139,422 B2 * | 11/2006 | Hauck et al. | 382/141 |
| 2005/0239221 A1 * | 10/2005 | Feng et al. | 438/14 |
| 2006/0130566 A1 * | 6/2006 | Wu | 73/82 |
| 2010/0229637 A1 * | 9/2010 | Konaka et al. | 73/81 |

* cited by examiner

*Primary Examiner* — Lisa Caputo
*Assistant Examiner* — Jamel Williams
(74) *Attorney, Agent, or Firm* — Raymond Y. Chan; David and Raymond Patent Firm (57) ABSTRACT

A testing machine includes a stand and a test device. The stand includes a base, box frame, a slide device driven to slide by a motor, and a control system controls the force applied on the test specimen. The test device is coupled at the slide device for performing various hardness tests consisting of Rockwell hardness test, Vickers hardness test, Brinell hardness test, micro-hardness test, and tension-compression test. The test device includes a force sensor and a data processing circuit converting an analog signal of the force sensor into digital data to interface with the control system.

53 Claims, 11 Drawing Sheets

UNIVERSAL TESTING MACHINE

CROSS REFERENCE OF RELATED APPLICATION

This is a non-provisional application that claims the benefit of priority under 35 U.S.C. §119 to a provisional application, application No. 61/283,902, filed Dec. 9, 2009.

BACKGROUND OF THE PRESENT INVENTION

1. Field of Invention

The present invention relates to a material hardness and tension and/or compression measuring device, and more specifically to a penetration hardness tester, which allows the user to measure, to high precision, the hardness of materials using many types of hardness tests.

2. Description of Related Arts

Well-known to those in the field, a lab needs many kinds of material testing machines, such as a Rockwell hardness tester, a Brinell hardness tester, a Vickers hardness tester, a Micro hardness tester and a Knoop hardness tester, as well as tension and compression testing machines. All manufacturers want to make a machine that can perform the same functions as many of if not all of the above machines, so that they can reduce machines quantities and costs. Until now, this is very difficult. All machines need to apply and measure precise and accurate forces and each machine has different amounts of force. For example, a Rockwell tester needs 10 kg force for minor forces and 150 kg for major forces, the Brinell tester needs a maximum force of 3000 kg, and micro Vickers tester needs precisely 0.1 kg force. Until now, a machine that can apply such a large range of forces accurately and precisely is not possible.

Even in a narrow range, machines have difficulty applying precise and accurate forces. For example, a Rockwell test requires 150 kg force. Using a 150 kg deadweight is too heavy for a lab machine, so designers use a 15 kg deadweight to apply a 150 kg force through levers. Because these mechanical parts will wear down over time, the force will eventually be inaccurate.

After the indenter penetrates to some depth or displacement in the test specimen, a measurement is made of the displacement. In prior art penetration hardness testers, there are moving mechanical parts which move relative to each other located between the actual displacement and measured displacement. Such relative mechanical movement can contribute to sources of friction or lost (non-recoverable) displacement between the point of displacement measurement and the test specimens so as to impair the repeated accuracy of the hardness test.

The use of deadweight testers and their mechanical impreciseness over time has led to the use of feedback control closed loop systems including a load cell as part of the means to measure the application of force to the test specimen.

U.S. Pat. No. 4,435,976 describes the use of a load cell to determine the forces applied during Brinell tests and employs a feedback loop to automatically compensate factors which affect the accuracy of the measurements, such factors being temperature and friction.

Another instance U.S. Pat. No. 6,142,010 describes the use of control closed loop systems including a load cell to measure and apply force for a Rockwell tester.

Another instance U.S. Pat. No. 6,247,356 describes the use of control closed loop systems including a load cell to measure and apply force for a micro hardness tester.

These apparatuses employ load cells as sensors to measure applied force. The weakness is they can only be used for one kind of hardness test. For example, the Rockwell tester cannot for be used for Vickers, Brinell or Micro hardness tests. Another weakness is these testers employ pancake load cells. This kind of load cell is only accurate to 0.1% to 0.5%. So, they cannot be used for measuring across a large range of forces.

U.S. Pat. No. 6,142,010 and U.S. Pat. No. 6,247,356 utilize a structure that does not provide enough support to withstand larger applied forces. This influences measurement accuracy.

All known bottom-referencing type hardness testing machines, using both load cell and deadweight style, employ an elevating screw to accommodate different specimen sizes. The mechanical forces employed in the elevating screw also can contribute to degradation of displacement measurement accuracy because of the possibility of additional deflection loss which can contribute to the inaccuracy of the displacement measurement.

All known prior hardness testers are not suitable to test holes or groove shaped specimens.

SUMMARY OF THE PRESENT INVENTION

Accordingly, it is an object of this invention to provide a new concept testing machine which performs all types of hardness testing: Rockwell, Brinell, Vickers, Micro Vickers and Knoop, and strength testing.

This tester of the present invention is conceptually different from previous testers. Instead of a single device of prior testers, this invention separates the testing and force applying phases into distinct devices.

An object of the present invention is to provide an apparatus with easy operation and highly accurate measurements. The apparatus is capable of automatically performing measurements.

Another object of this invention is to provide such an apparatus which advantageously employs new technology including electronics to communicate with a computer.

Another object of the invention is to provide a machine that is capable of easily switching between types of hardness tests such as Rockwell, Brinell, Vickers, Micro Vickers, Knoop and strength.

Another object of the invention is to provide a testing machine upon which it is easy to mount and replace different test devices and different indenters.

Another object of the invention is to provide a testing machine with a simpler structure, so there are lower costs and less maintenance.

Another object of the invention is to provide a testing machine, wherein the test device is an independent unit which comprises the force sensor, displacement sensor and data processing circuit.

Another object of the invention is to provide a testing machine, wherein the force sensor of the test device is much more precise than prior hardness testers. In particularly, the force sensor of the test device is a beam type load cell.

Another object of the invention is to provide a testing machine, wherein the test device directly measures the displacement of the indenter at the surface of the specimen. This reduces displacement errors from transfer displacements. The displacement sensor of the test device is a capacitive type sensor or the optical grating sensor or Linear Variable Differential Transformer sensor.

Another object of the invention is to provide a testing machine, wherein the structure of the test device is suitable for testing holes, grooves or other anomalously shaped specimens.

Another object of the invention is to provide a testing machine, wherein the data processing circuit of the test device converts the analog signal of the force sensor and displacement sensor into digital data and then sends it through the interface to the control and display system.

Another object of the invention is to provide a testing machine, wherein the data process circuit has data storage function, so the test device can store all data including its own identification and calibration data. When the test device is installed with different force devices, the test results will be the same for the same specimen, regardless of force device.

Another object of the invention is to provide a testing machine, wherein the force device applies high accuracy tension and compression forces across a large range from 0.01 kg to 1000 kg.

Another object of the invention is to provide a testing machine, wherein the force device includes a box frame, base, and slide block. The box frame fixes two rods and one ball screw. An AC servo motor is fixed onto the bottom table and connects to the ball screw. It drives the ball screw which moves the slide block vertically along the rods.

Another object of the invention is to provide a testing machine, wherein the slide block has a slot for installing a test device. In the slot is a circuit interface to communicate with the test device.

Another object of the invention is to provide a testing machine, wherein the surface of the force device's base is a table with a T-slot. The anvil for holding specimens is installed on the table by screws. Different shape anvils can be installed and switched according to specimen shape. Also, the base's table itself can support large specimens. This structure eliminates the need for elevating screws to accommodate different specimen sizes and also avoids the inaccuracy caused by the elevating screw structure.

According to the present invention, the foregoing and other objects and advantages are attained by providing a testing machine, comprising:

a plurality of test devices for performing various hardness tests selected from the group consisting of Rockwell hardness test, Vickers hardness test, Brinell hardness test, micro-hardness test, and tension-compression test, wherein each of the test devices is an individual unit that each of the test devices comprises its own force sensor and its own data processing circuit; and a stand comprising means for power generation, a slide device driven to slide by the power generation means, and a control system operatively linked to the test device when the test device is coupled at the slide device for controlling a force applied on the test specimen, wherein the test devices are replaceably and detachably coupled at the slide device to perform the corresponding hardness tests, such that by selectively switching test devices are selectively switched from one to another, the testing machine forms a universal testing apparatus for performing the different hardness test of a test specimen.

In accordance with another aspect of the invention, the present invention provides a method of testing a test specimen via a testing machine, comprising the steps of:

(a) selecting one of test devices in order to perform one of hardness test on the test specimen, wherein the hardness tests are selected from the group consisting of Rockwell hardness test, Vickers hardness test, Brinell hardness test, micro-hardness test, and tension-compression test;

(b) detachably coupling the test device at a slide device of a stand to perform the particular hardness test, wherein each of the test devices comprises its own force sensor and its own data processing circuit;

(c) controlling a force applied on the test specimen via a control system; and (d) sending a digital data of the force sensor to interface with the control system.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
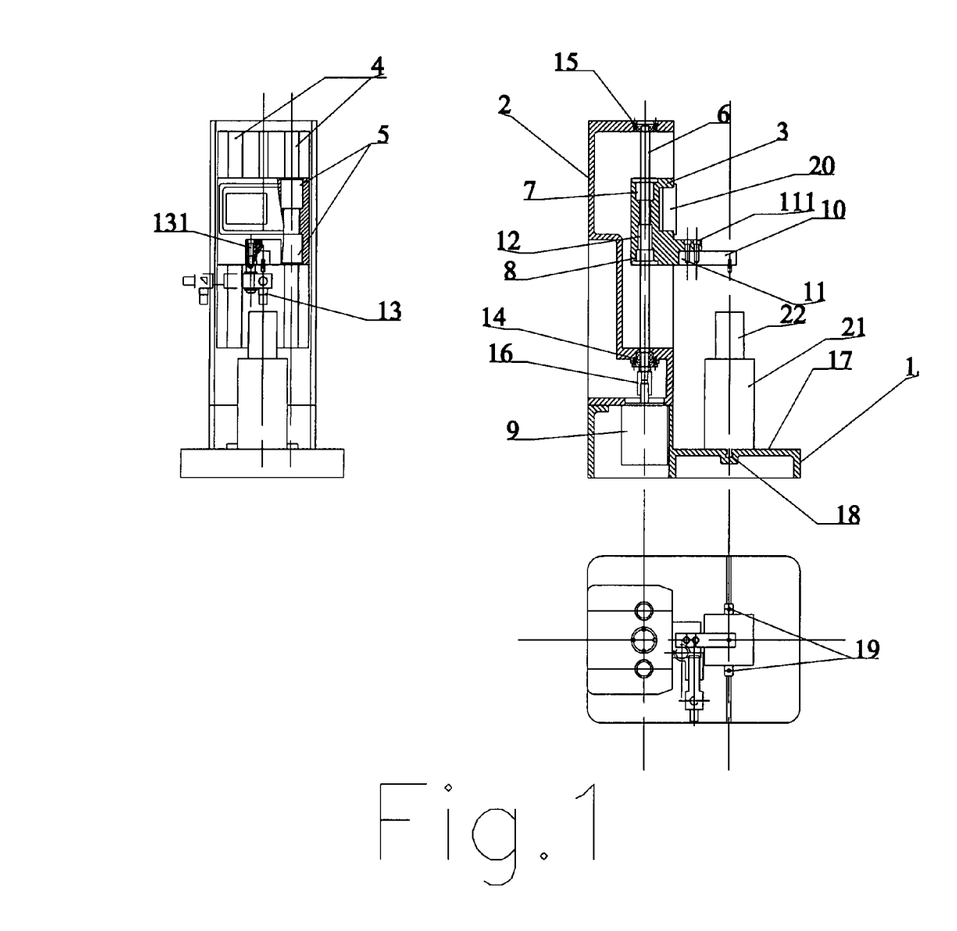
FIG. 1 is a view of the testing machine according to a preferred embodiment of the present invention.

Description will now be given of the inventive testing machine with reference to FIG. 1. As shown in FIG. 1, the inventive testing machine comprises a stand which comprises a base 1 and a box frame 2. Box frame 2 is fixed to the base 1 and base 1 serves as the structural foundation of the testing machine. Movement of the Slide device 3 is accomplished by controlling an AC servo motor 9 located at the bottle of the box frame 2. The motor 9 drives a threaded ball screw 6. A pair of guide shafts 4 straddles ball screw 6. Round bearings or slide members 5 along the guide shafts 4 permit movement of the slide device 3. The slide device 3 is moved by the ball screw 6.

The motor 9 connects rigidly to the ball screw 6 by a shaft coupling 16. The ball screw 6 mounts on box frame 2 by bearings 14 and 15.

The ball nut 7 is fixed on slide device 3. Another ball nut 8 is attached on the slide device 3. This ball nut 8 has a slight freedom of movement vertically. A spring 12 is mounted on the slide device 3, between ball nut 7 and ball nut 8 to minimize backlash. This spring 12 minimizes the gap between ball nut and ball screw. When the motor 9 changes direction, i.e. from clockwise to counterclockwise or from counterclockwise to clockwise, the spring 12 will close any gaps that arise, thus canceling backlash.

The control and display system 20 is installed onto the slide device 3.

The surface of base 1 is a table 17 with a T-slot 18. The anvil 21 is affixed on table 17 by screws 19. The specimen 22 is placed on the anvil 21. Different shaped anvils 21 can be switched according to specimen shape. Also, the table 17 itself can support big specimens if required without the need for the anvil 21.

Figure 11:
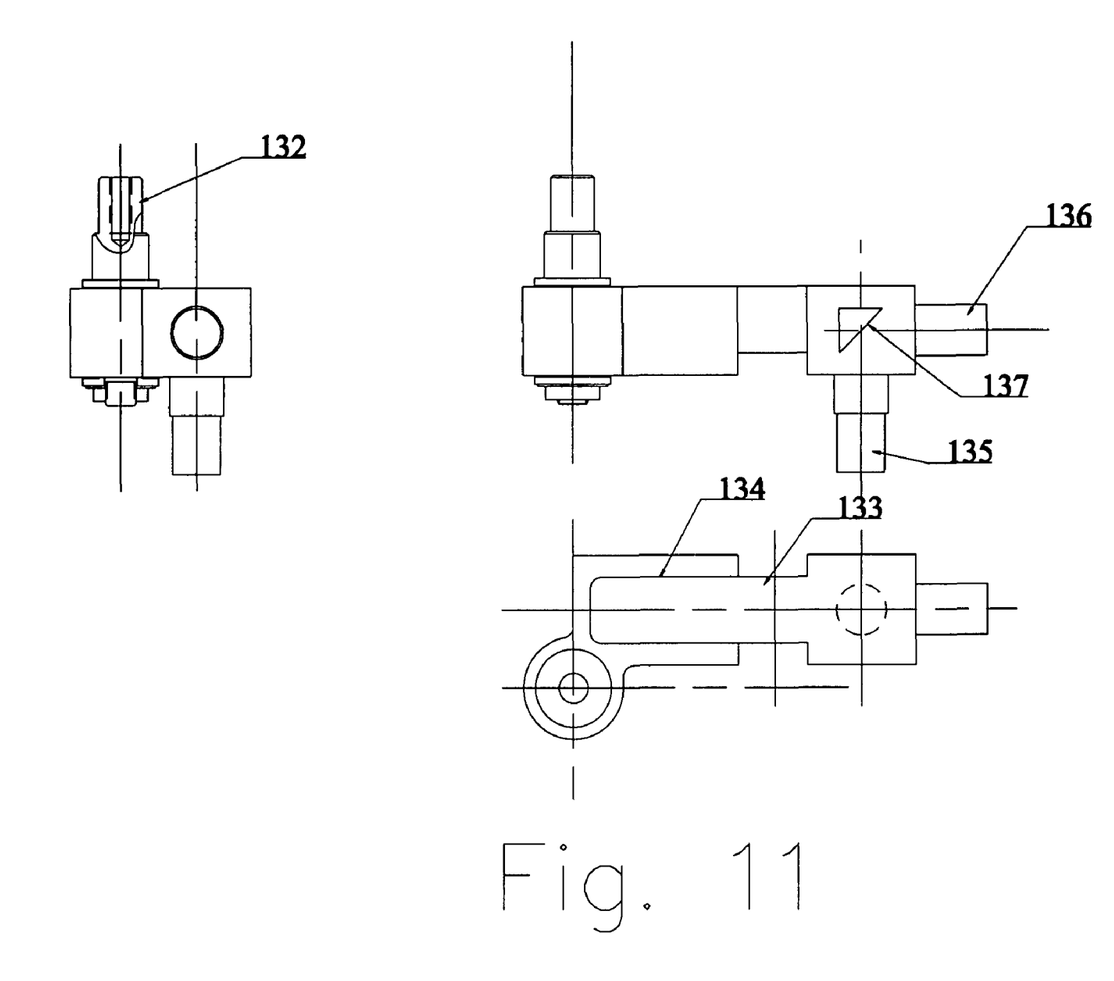
FIG. 11 is a view of microscope of the testing machine according to the above preferred embodiment of the present invention.

The testing machine further comprises one microscope 13 which is supported by the slide device 3 of the testing machine. FIG. 11 describes the microscope which is used with Vickers test device or Microhardness test device. The user of the testing machine may use microscope 13 to view a specimen 22 on anvil 21 in a magnified fashion so as to examine indentations made by the indenters. The shaft 132 of the microscope 13 is fixed on slide device 3 by a screw 131 shown in FIG. 1. The microscope 13 rotates about the shaft 132 to switch from work position to idle position. This microscope 13 can be adjusted automatically or manually. The body 133 of the microscope installed in a groove 134 and can move slightly so the microscope position can be adjusted to center the objective 135 on the indentation on specimen 22. The objective 135 and the eyepiece 136 are on the body 133 of the microscope. The image of the indentation on the specimen 22 reflects through objective 135 and off mirror 137 into eyepiece 136. The user of the testing machine may switch the eyepiece 136 with a digital camera that has a CCD or CMOS optical sensor.

The test device 10 of the testing machine is installed in the groove 11 of slide device 3 by screws 111. There are many kinds of test devices 10 that are able to be attached on the test machine: Rockwell test device FIG. 2, Vickers test device FIG. 5, Brinell device FIG. 6, microhardness test device FIG. 7 and tension or compression test device FIG. 8. Each test device is an independent unit with its own force sensor, displacement sensor and data processing circuit. In other words, the present invention forms a universal testing apparatus for performing different hardness tests in one machine.

Figure 2:
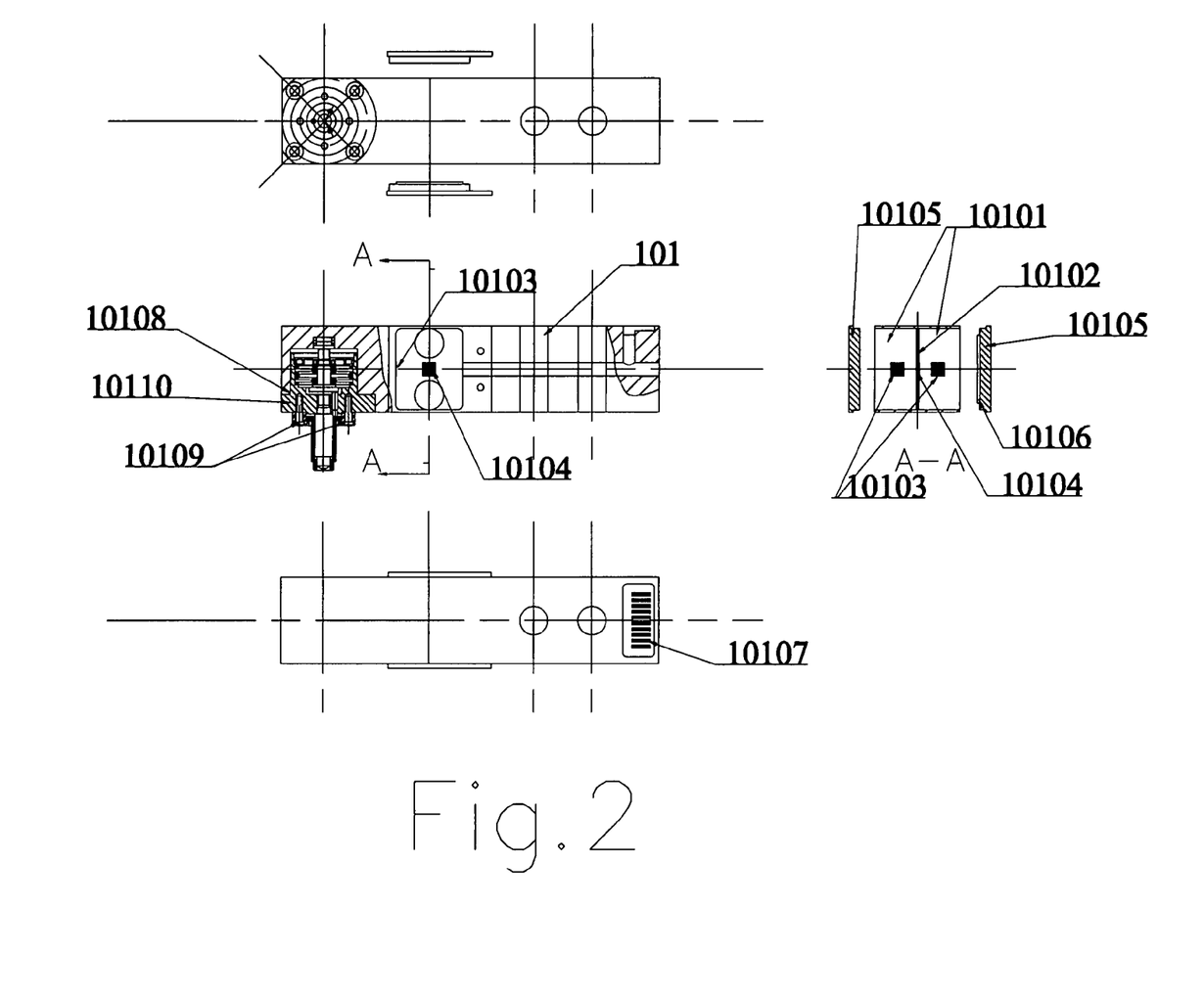
FIG. 2 is a view of the Rockwell hardness test device of the testing machine according to the above preferred embodiment of the present invention.

FIG. 2 describes a Rockwell test device 101. Both sides of the body 101 of the Rockwell test device 101 have rectangular shaped chambers 10101 that form a wall 10102 therebetween. Two strain gauges 10103 stick on the chambers' 10101 side, and another two strain gauges 10104 stick on each side of the wall 10102. This forms a beam type load cell and is a very high accuracy force sensor with errors of only 0.02% in nonrepeatability, hysteresis and nonlinearity, which are better than a pancake load cell's errors. The full measurement range of the Rockwell test device 101 is 150 kg.

The receiving chamber 10108 at the front of the body 101 of the Rockwell test device 101 holds a displacement sensor 10110 by 4 pieces screw 10109. The displacement sensor is for measuring the depth of the indentation on the test specimen 22.

Figure 3:
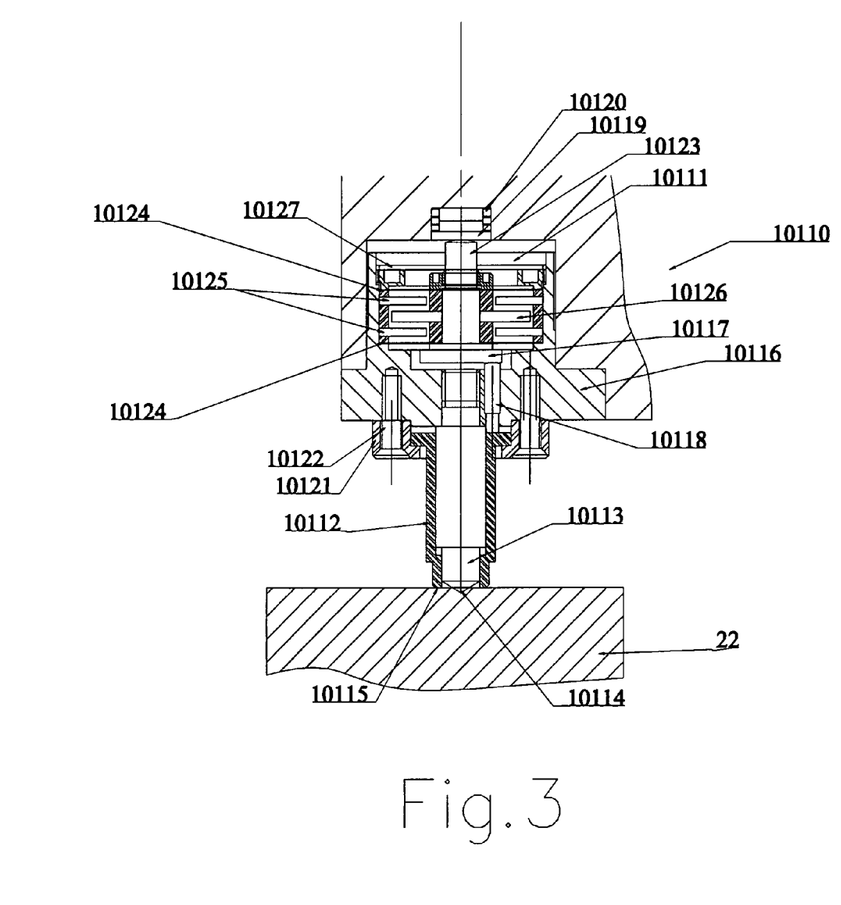
FIG. 3 is a view of the displacement sensor of the Rockwell hardness test device of the testing machine according to the above preferred embodiment of the present invention.

FIG. 3 describes the displacement sensor. The displacement sensor 10110 has a pin receiving chamber 10111 and a penetrating pin 10113 coaxially disposed in the flange 10116 of displacement sensor 10110. The tubular guiding cylinder 10112 encloses the penetrating pin 10113. It permits the penetrating pin 10113 to move only vertically to coaxially align the penetrating pin 10113 and prevents horizontal movement from the applied force on the pin head 10114 penetrating the surface of the test specimen 22.

The displacement sensor 10110 of the Rockwell device 101 further comprises a sensor shaft 10123 movably disposed in the pin receiving chamber 10111. Three pieces transmission pins 10118 are placed between the guiding cylinder 10112 and the bottom 10117 of the sensor shaft 10123. The three transmission pins 10118 are placed in a circular fashion, 120 degrees apart, across the bottom 10117 of the sensor shaft 10123. When the slide device 3 is driven to apply a force on the penetrating pin head 10114 to penetrate the testing surface of the test specimen 22, the guiding cylinder 10112 moves up and in turn, drives the three transmission pins 10118 and drives sensor shaft 10123. The displacement sensor 10110 then detects and measures a linear displacement of the sensor shaft 10123 with respect to the penetrating pin 10113 for indicating the hardness of the test specimen 22.

As shown in FIG. 3, the opening edge 10115 of the guiding cylinder 10112 has a flat surface for lying flush against the testing surface of the test specimen 22 to ensure high accuracy in the displacement measurement.

Therefore, the test specimen 22 requires a relatively small testing surface in a flat manner that enough of the opening edge 10115 of the guiding cylinder 10112 to flatten thereon in such a manner that the guiding cylinder 10112 is guided to coaxially slide along the penetrating pin 10113 to precisely measure the displacement of penetrating pin head 10114 penetrating the testing surface of the tested specimen 22.

The displacement sensor 10110 further comprises a wave spring 10120 and a spring supporter 10119 disposed within the body 101 of the Rockwell test device 101 for applying a force against the sensor shaft 10123, and in turn, against the transmission pins 10118, and in turn, against the guiding cylinder 10112 to provide resistance and to retain the guiding cylinder 10112 in a zero-displacement testing position when there is no specimen.

The displacement sensor 10110 further comprises a cover flange 10121 fixed onto the flange 10116 by 4 pieces screws 10122 which limits the moving distance of the guiding cylinder 10112 along the penetrating pin 10113.

The displacement sensor 10110 further comprises two round steel leaves 10124, which is fixed at the outer edge by the pin receiving chamber 10111 of the flange 10116. The two round steel leaves' inner holes are fixed at the sensor shaft 10123. This structure, fixed at both the outer edge and the inner hole, prevents the sensor shaft 10123 from moving horizontally, ensuring only vertical movement. The lack of horizontal movement of the steel leaves 10124 takes away a source of noise.

The displacement sensor 10110 further comprises two fixed electrical terminals 10125 fixed within the pin receiving chamber 10111, and one moveable electrical terminal 10126 fixed by the sensor shaft 10123. When the sensor shaft 10123 is displaced, the moveable electrical terminal 10126 moves between both fixed electrical terminals 10125. The two fixed terminals 10125 and one moveable terminal 10126 form into two capacitances. The two capacitances between the two fixed terminals 10125 and one moveable terminal 10126 vary as the sensor shaft 10123 moves, the difference of the two capacitances is proportional to the vertical displacement of the sensor shaft 10123, this signal is in turn proportional to the displacement of the penetrating pin head 10114 caused by penetrating the testing surface of the tested specimen 22.

The displacement sensor 10110 further comprises one capacitance conditioner circuit 10127 which is located in the pin receiving chamber 10111 and converts a capacitance signal to an amplified analog signal.

Another option for the displacement sensor is to use an optical grating sensor. When the cost of an optical grating sensor decreases, this grating sensor will be suitable.

Another option for the displacement sensor is to use a Linear Variable Differential Transformer sensor. When the sensor precision, resolution, and sensitivity for this technology is increased, this Linear Variable Differential Transformer sensor can be used.

Figure 4:
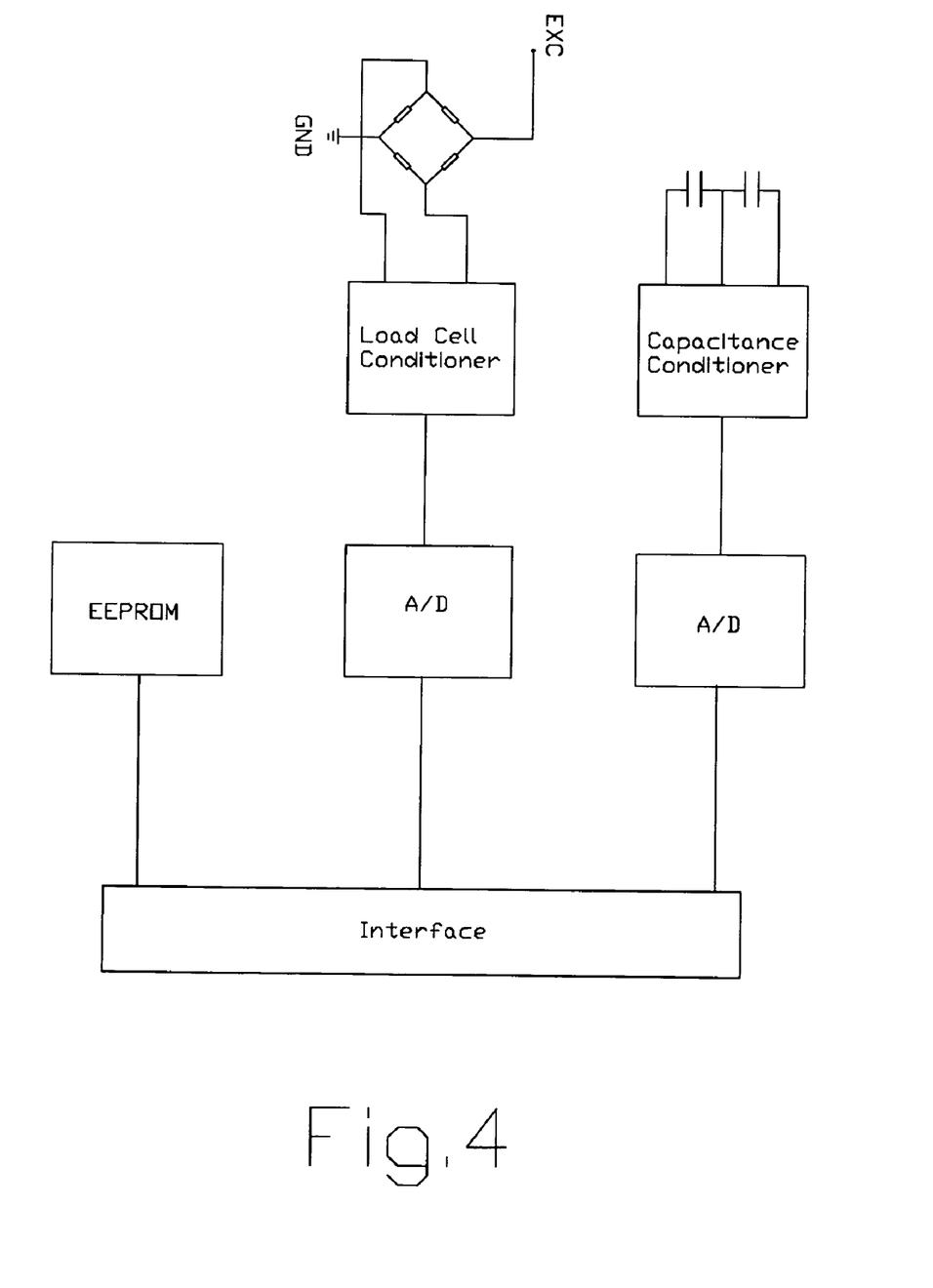
FIG. 4 is an electronics circuit block and schematic diagram of the Rockwell hardness test device of the testing machine according to the above preferred embodiment of the present invention.

The Rockwell device further comprises two side covers 10105 of test device body 101 in FIG. 2. The circuit 10106 is affixed to the right hand side cover. FIG. 4 is an electronics circuit block and schematic diagram of the Rockwell hardness test device 101. The circuit of the test device converts the analog signal of the force sensor and displacement sensor into digital data to interface with the control and display systems.

The circuit has data memory EEPROM, so the test device can store all data including its own identification and all calibration data. So, all test devices are independent and can be installed on any testing machine and still the test results will be consistently the same for the same specimen regardless of testing machine. There will be no need to recalibrate the entire tester when the test device is installed onto a different tester or force device.

The Rockwell test device 101 further comprises one connect interface 10107, shown in FIG. 2, which contacts the interface on slide device 3 and through this interface the Rockwell hardness test device 101 communicates with control and display system.

Figure 5:
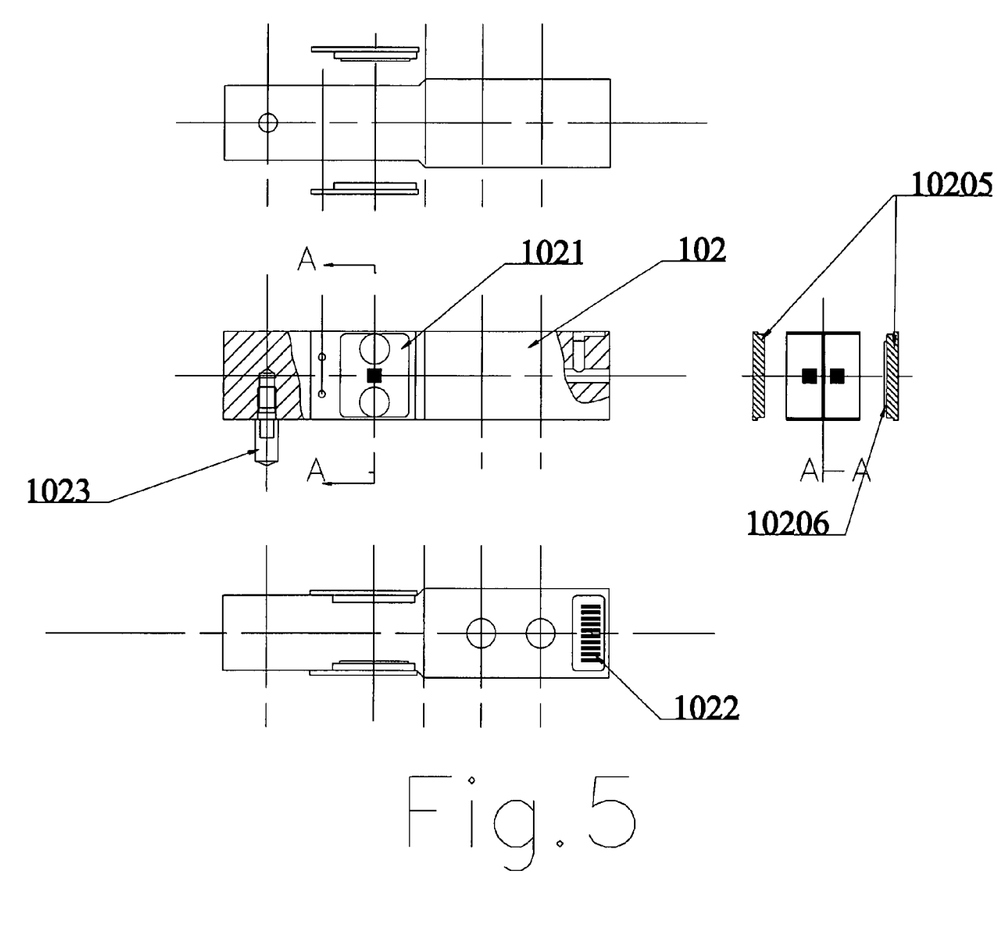
FIG. 5 is a view of the Vickers hardness test device of the testing machine according to the above preferred embodiment of the present invention.
Figure 9:
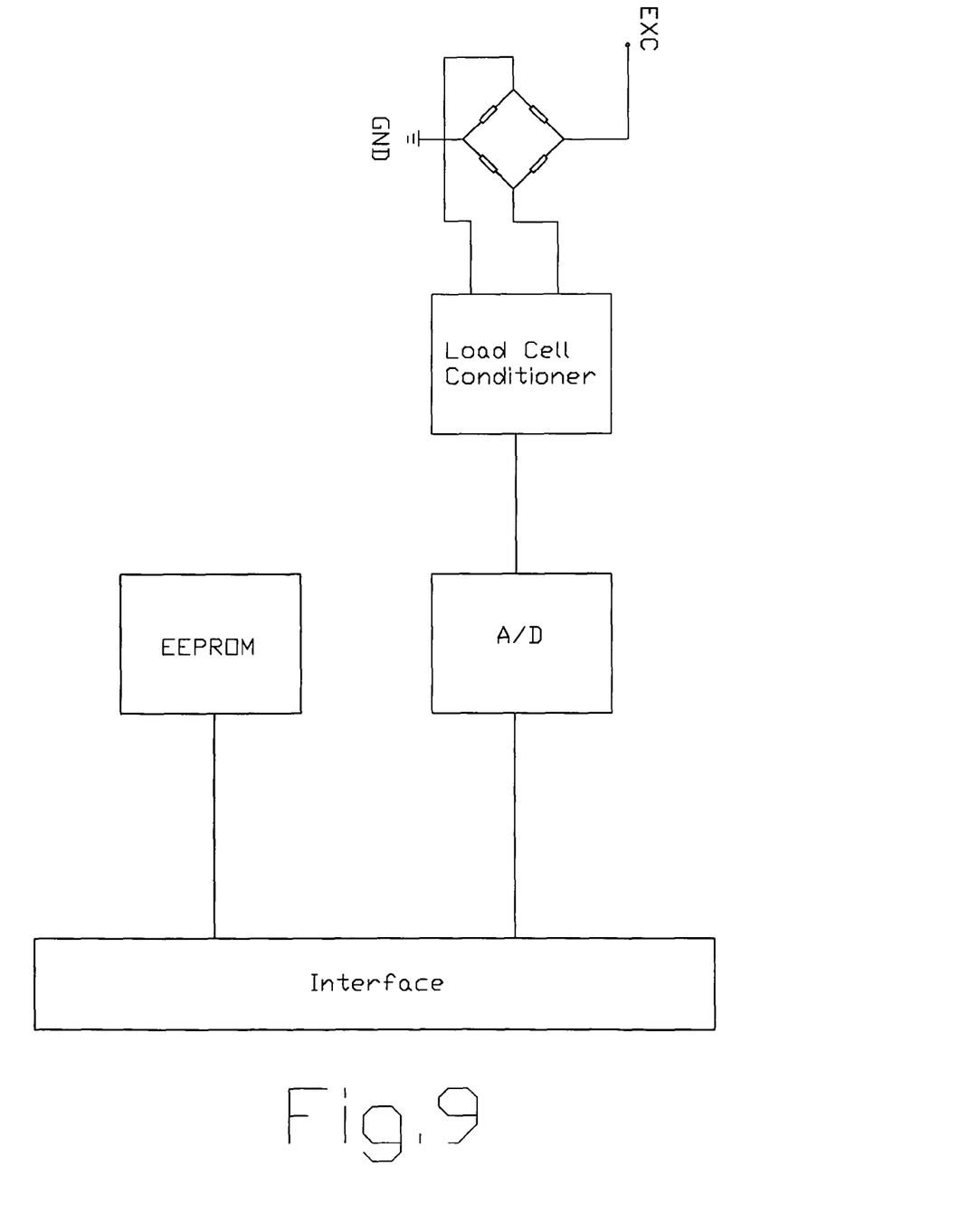
FIG. 9 is an electronics circuit block and schematic diagram of other test devices (Brinell, Vickers, Micro hardness, tension and/or compression) of the testing machine according to the above preferred embodiment of the present invention.

FIG. 5 describes a Vickers test device 102. The Vickers test device 102 comprises one force sensor 1021, the Vickers penetrating pin 1023, one connect interface 1022 and one circuit 10206. FIG. 9 is an electronic circuit block diagram and schematic of the Vickers hardness test device 102. The circuit of the test device converts the analog signal of the force sensor into digital data to interface with the control unit.

The circuit has data memory EEPROM, so that the test device can store all data including its own identification and all calibration data. So, all test devices are independent and can be installed on any testing machine and still the test results will be consistently the same for the same specimen regardless of testing machine. There will be no need to recalibrate the entire tester when the test device is installed onto a different tester or force device.

The force sensor principle is same as the Rockwell test device. The full measurement range of the Vickers test device 102 is 120 kg. The Vickers test device 102 is used together with microscope 13 shown in FIG. 11.

Figure 6:
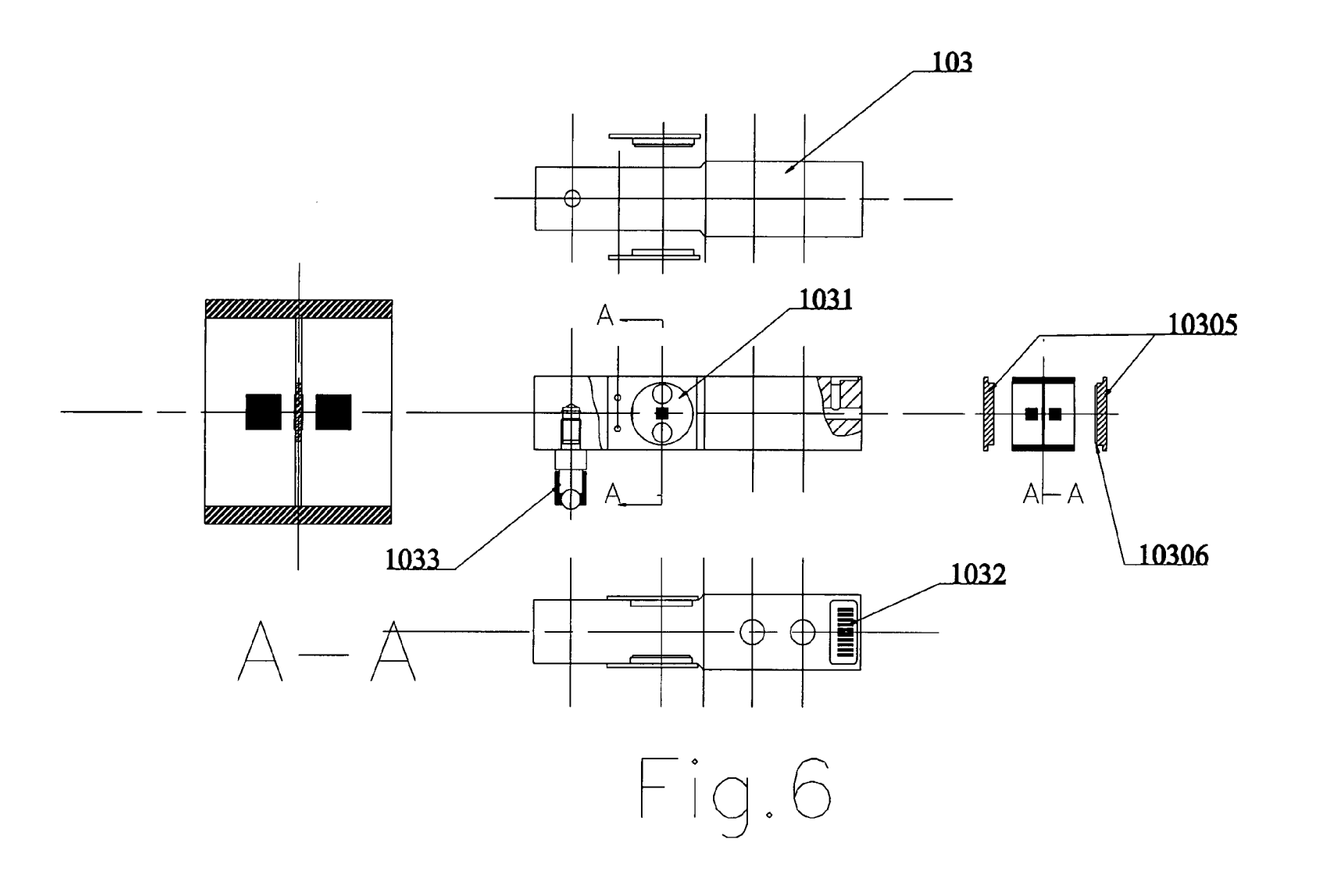
FIG. 6 is a view of the Brinell hardness test device of the testing machine according to the above preferred embodiment of the present invention.

FIG. 6 describes a Brinell test device 103. The Brinell test device 103 comprises one force sensor 1031, one ball penetrating pin 1033, one connect interface 1032 and one circuit 10306. FIG. 9 is an electronic circuit block diagram and schematic of the Brinell hardness test device 103. The circuit of the test device converts the analog signal of the force sensor into digital data to interface with the control unit.

The circuit has data memory EEPROM, so that the test device can store all data including its own identification and all calibration data. So, all test devices are independent and can be installed on any testing machine and still the test results will be consistently the same for the same specimen regardless of testing machine. There will be no need to recalibrate the entire tester when the test device is installed onto a different tester or force device.

The force sensor shape of the Brinell test device 103 is different from the Rockwell force sensor's. The testing principle is same as the Rockwell test device. The full measurement range of the Brinell test device 103 is up to 3000 Kg. The Brinell test device 103 is used together with microscope 13.

Figure 7:
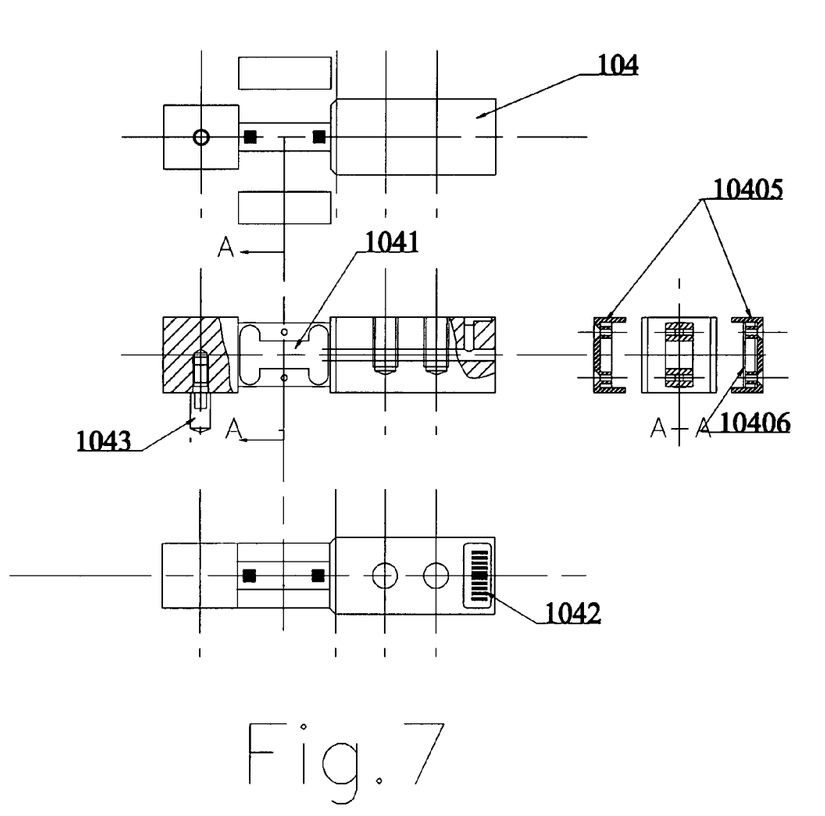
FIG. 7 is a view of the Micro hardness test device of the testing machine according to the above preferred embodiment of the present invention.

FIG. 7 describes a microhardness test device 104 used for micro Vickers and Knoop hardness testing. The microhardness test device 104 comprises one force sensor 1041, the micro Vickers or Knoop penetrating pin 1043, one connect interface 1042 and one circuit 10406. FIG. 9 is an electronic circuit block diagram and schematic of the microhardness test device 104. The circuit of the test device converts the analog signal of the force sensor into digital data to interface with the control unit.

The circuit has data memory EEPROM, so that the test device can store all data including its own identification and all calibration data. So, all test devices are independent and can be installed on any testing machine and still the test results will be consistently the same for the same specimen regardless of testing machine. There will be no need to recalibrate the entire tester when the test device is installed onto a different tester or force device.

The force sensor shape of microhardness test device 104 is different from Rockwell force sensor's. The testing principle is the same as the Rockwell test device. The full measurement range of the Microhardness test device 104 is 5 kg. The Microhardness test device 104 is used together with microscope 13.

Figure 8:
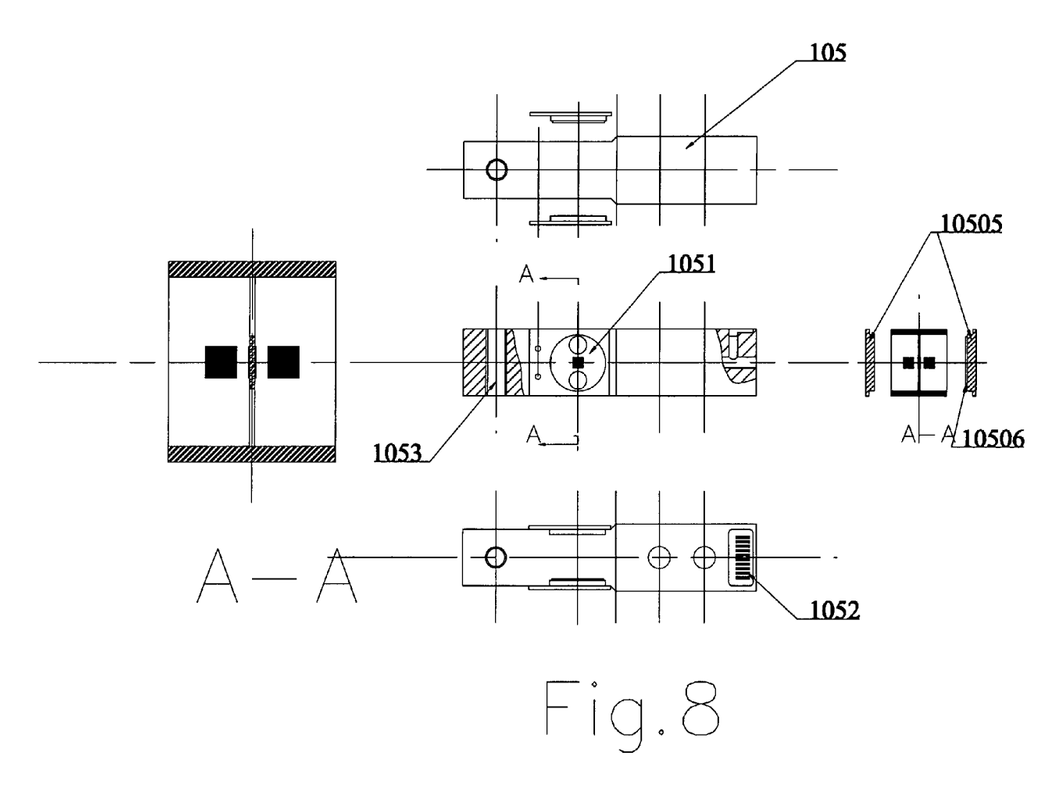
FIG. 8 is a view of the tension and/or compression test device of the testing machine according to the above preferred embodiment of the present invention.

FIG. 8 describes a tension or compression test device 105. The tension or compression test device 105 comprises one force sensor 1051, the thread hole 1053 for tension or compression measurement, one connect interface 1052 and one circuit 10506. FIG. 9 is an electronic circuit block diagram and schematic of the tension or compression test device 105. The circuit of the test device converts the analog signal of the force sensor into digital data to interface with the control unit.

The circuit has data memory EEPROM, so that the test device can store all data including its own identification and all calibration data. So, all test devices are independent and can be installed on any testing machine and still the test results will be consistently the same for the same specimen regardless of testing machine. There will be no need to recalibrate the entire tester when the test device is installed onto a different tester or force device.

The force sensor of the tension or compression test device 105 is the same as the Brinell force sensor. The full measurement range of the tension or compression test device 105 is up to 3000 Kg.

Figure 10:
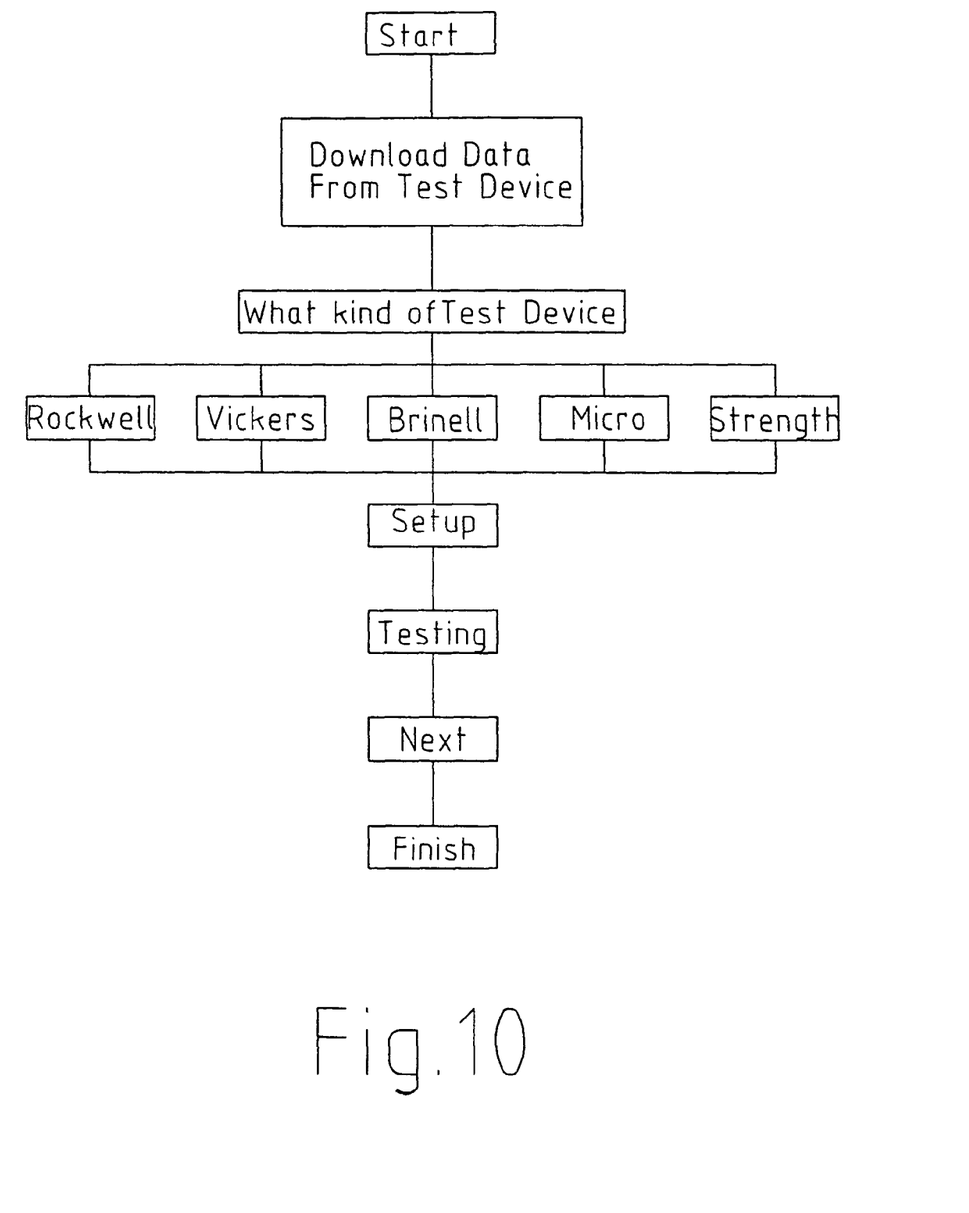
FIG. 10 is a flowchart of the operation of the testing machine according to the above preferred embodiment of the present invention.

FIG. 10 is a flowchart of the testing machine.

First, the user selects a test device 10 according to hardness test required and installs it on the slide device. Then, the user turns on the power. The control and display system automatically download data from memory of test device 10 including identification, calibration information and type of test device. The control and display system automatically setup according to type of test device 10. For instance, when performing a Rockwell test, the AC servo motor 9 drives ball screw 6, the slide device 3 moves towards the test specimen 22, when the pin head 10114 of the penetrating pin 10113 perpendicularly penetrates the testing surface of the test specimen 22, the strain gage 10103 measures the force of the pin head 10114 on test specimen and sends the measurement result to the control and display system 20. The control and display system will, according to measurement results, command the motor to continue driving the ball screw and slide device until the required force is reached. After the pin head 10114 of the penetrating pin 10113 perpendicularly penetrates the testing surface of the test specimen 22, the guiding cylinder 10112 of Rockwell test device 101 moves up, and the displacement sensor 10110 measures the depth of indentation.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A testing machine, comprising:
   a plurality of test devices for performing various hardness tests selected from the group consisting of Rockwell hardness test, Vickers hardness test, Brinell hardness test, micro-hardness test, and tension-compression test, wherein each of said test devices is an individual unit that each of said test devices comprises its own force sensor and its own data processing circuit; and
   a stand comprising means for power generation, a slide device driven to slide by said power generation means, and a control system operatively linked to said test device when said test device is coupled at said slide device for controlling a force applied on said test specimen, wherein said test devices are replaceably and detachably coupled at said slide device to perform said corresponding hardness tests, such that by selectively switching test devices are selectively switched from one to another, said testing machine forms a universal testing apparatus for performing said different hardness test of a test specimen.

2. The testing machine, as recited in claim 1, wherein one of said test devices is a Rockwell test device which comprises a beam type load cell as a force sensor and a sensor operating therewithin, wherein said sensor selected from the group consisting of a displacement sensor, an optical grating sensor and a Linear Variable Differential Transformer sensor.

3. The testing machine, as recited in claim 2, wherein said displacement sensor comprises a penetrating pin enclosed within a tubular guiding cylinder for permitting a penetrating pin head of said penetrating pin to move only vertically to penetrate on a surface of the test specimen, and a sensor shaft arranged in such a manner that when said slide device is driven to apply a force on said penetrating pin head to penetrate on the surface of the test specimen, said displacement sensor detects and measures a linear displacement of said sensor shaft with respect to said penetrating pin for indicating the hardness of the test specimen.

4. The testing machine, as recited in claim 3, wherein said beam type load cell has two chambers defining a wall therebetween, and comprising two first strain gauges supported within said two chambers respectively and two second strain gauges supported at two sides of said wall to form said beam type load cell.

5. The testing machine, as recited in claim 4, wherein said Rockwell test device further has a pin receiving chamber for said sensor shaft movably disposed therein and comprises three transmission pins being placed between said guiding cylinder and a bottom of said sensor shaft and placed in a circular fashion, 120 degrees apart, across said bottom of said sensor shaft, such that when said slide device is driven to apply the force on said penetrating pin head for penetrating the surface of the test specimen, said guiding cylinder moves up and in turn, drives said three transmission pins and drive sensor shaft, so as to enable the linear displacement of said sensor shaft being detected and measured by said displacement sensor with respect to said penetrating pin.

6. The testing machine, as recited in claim 5, wherein an opening edge of said guiding cylinder has a flat surface for lying flush against the surface of the test specimen to ensure high accuracy in the displacement measurement.

7. The testing machine, as recited in claim 6, wherein said displacement sensor further comprises a wave spring and a spring supporter disposed therewithin for applying a force against said sensor shaft, and in turn, against said transmission pins, and in turn, against said guiding cylinder to provide resistance and to retain said guiding cylinder in a zero-displacement testing position when there is no specimen.

8. The testing machine, as recited in claim 7, wherein said displacement sensor further comprises two round steel leaves, which is fixed at an outer edge by said receiving chamber of a flange, wherein said two round steel leaves' inner holes are fixed at said sensor shaft to prevent said sensor shaft from moving horizontally and to ensure only vertical movement.

9. The testing machine, as recited in claim 8, wherein said displacement sensor further comprises two fixed electrical terminals fixed within said pin receiving chamber, and one moveable electrical terminal fixed by said sensor shaft, wherein when said sensor shaft is displaced, said moveable electrical terminal moves between both fixed electrical terminals while said two fixed terminals and one moveable terminal form into two capacitances, wherein said two capacitances between said two fixed terminals and one moveable terminal vary as said sensor shaft moves, the difference of said two capacitances is proportional to the vertical displacement of said sensor shaft.

10. The testing machine, as recited in claim 9, wherein said displacement sensor further comprises one capacitance conditioner circuit which is located in said receiving chamber and converts a capacitance signal to an amplified analog signal.

11. The testing machine, as recited in claim 2, wherein said Rockwell test device further comprises a connect interface which contacts an interface on said slide device to communicatively link said Rockwell test device with said control system, wherein said data processing circuit of said Rockwell test device converts an analog signal of said force sensor and said displacement sensor into digital data to interface with said control system.

12. The testing machine, as recited in claim 10, wherein said Rockwell test device further comprises a connect interface which contacts an interface on said slide device to communicatively link said Rockwell test device with said control system, wherein said data processing circuit of said Rockwell test device converts an analog signal of said force sensor and said displacement sensor into digital data to interface with said control system.

13. The testing machine, as recited in claim 1, wherein one of said test devices is a Vickers test device which comprises a force sensor, a Vickers penetrating pin for penetrating on the surface of the test specimen, and a connect interface contacting an interface on said slide device to communicatively link said Vickers test device with said control system, wherein said data processing circuit of said Vickers test device converts an analog signal of said force sensor into digital data to interface with said control system.

14. The testing machine, as recited in claim 12, wherein one of said test devices is a Vickers test device which comprises a force sensor, a Vickers penetrating pin for penetrating on the surface of the test specimen, and a connect interface contacting an interface on said slide device to communicatively link said Vickers test device with said control system, wherein said data processing circuit of said Vickers test device converts an analog signal of said force sensor into digital data to interface with said control system.

15. The testing machine, as recited in claim 13, wherein a full measurement range of said Vickers test device is 120 kg.

16. The testing machine, as recited in claim 14, wherein a full measurement range of said Vickers test device is 120 kg.

17. The testing machine, as recited in claim 1, wherein one of said test devices is a Brinell test device which comprises a force sensor, a ball penetrating pin, and a connect interface contacting an interface on said slide device to communicatively link said Brinell test device with said control system, wherein said data processing circuit of said Brinell test device converts an analog signal of said force sensor into digital data to interface with said control system.

18. The testing machine, as recited in claim 16, wherein one of said test devices is a Brinell test device which comprises a force sensor, a ball penetrating pin, and a connect interface contacting an interface on said slide device to communicatively link said Brinell test device with said control system, wherein said data processing circuit of said Brinell test device converts an analog signal of said force sensor into digital data to interface with said control system.

19. The testing machine, as recited in claim 17, wherein a full measurement range of the Brinell test device is up to 3000 Kg.

20. The testing machine, as recited in claim 18, wherein a full measurement range of the Brinell test device is up to 3000 Kg.

21. The testing machine, as recited in claim 1, wherein one of said test devices is a microhardness test device which comprises a force sensor, a micro Vickers or Knoop penetrating pin, and a connect interface contacting an interface on said slide device to communicatively link said microhardness test device with said control system, wherein said data processing circuit of said microhardness test device converts an analog signal of said force sensor into digital data to interface with said control system.

22. The testing machine, as recited in claim 20, wherein one of said test devices is a microhardness test device which comprises a force sensor, a micro Vickers or Knoop penetrating pin, and a connect interface contacting an interface on said slide device to communicatively link said microhardness test device with said control system, wherein said data processing circuit of said microhardness test device converts an analog signal of said force sensor into digital data to interface with said control system.

23. The testing machine, as recited in claim 21, wherein a full measurement range of said Microhardness test device is 5 kg.

24. The testing machine, as recited in claim 22, wherein a full measurement range of said Microhardness test device is 5 kg.

25. The testing machine, as recited in claim 1, wherein one of said test devices is a tension-compression test device which comprises one force sensor, a thread hole for tension or compression measurement, and a connect interface contacting an interface on said slide device to communicatively link said tension-compression test device with said control system, wherein said data processing circuit of said tension-compression test device converts an analog signal of said force sensor into digital data to interface with said control system.

26. The testing machine, as recited in claim 24, wherein one of said test devices is a tension-compression test device which comprises one force sensor, a thread hole for tension or compression measurement, and a connect interface contacting an interface on said slide device to communicatively link said tension-compression test device with said control system, wherein said data processing circuit of said tension-compression test device converts an analog signal of said force sensor into digital data to interface with said control system.

27. The testing machine, as recited in claim 25, wherein a full measurement range of the tension or compression test device 105 is up to 3000 Kg.

28. The testing machine, as recited in claim 26, wherein a full measurement range of the tension or compression test device 105 is up to 3000 Kg.

29. A testing machine, comprising:
a stand comprising a base for supporting a test specimen thereat, a box frame supported on said base, a motor supported by said box frame for power generation, a slide device movably supported at said box frame and being powered to slide by said motor, and a control system provided at said slide device for controlling a force applied on the test specimen; and
a test device coupling with said slide device for performing a hardness test of the test specimen selected from the group consisting of Rockwell hardness test, Vickers hardness test, Brinell hardness test, micro-hardness test, and tension-compression test, wherein said test device comprises a force sensor and a data processing circuit converting an analog signal of said force sensor into digital data to interface with said control system.

30. The testing machine, as recited in claim 29, wherein said stand further comprises a ball screw movably coupled said slide device at said box frame, a first ball nut fixed on said slide device, a second ball nut attached on said slide device that said second ball nut has a slight freedom of movement vertically, and a spring mounted on said slide device between said first and second ball nuts to minimize backlash that said spring minimizes a gap between said ball nut and said ball screw.

31. The testing machine, as recited in claim 30, further comprising a microscope which is supported by said slide device and is rotated about a shaft of said microscope to switch from a work position to an idle position.

32. The testing machine, as recited in claim 29, wherein said test device is detachably coupled with said slide device.

33. The testing machine, as recited in claim 32, wherein said test device is a Rockwell test device which comprises a beam type load cell as said force sensor and a sensor operating therewithin, wherein said sensor selected from the group consisting of a displacement sensor, an optical grating sensor and a Linear Variable Differential Transformer sensor.

34. The testing machine, as recited in claim 33, wherein said displacement sensor comprises a penetrating pin enclosed within a tubular guiding cylinder for permitting a penetrating pin head of said penetrating pin to move only vertically to penetrate on a surface of the test specimen, and a sensor shaft arranged in such a manner that when said slide device is driven to apply a force on said penetrating pin head to penetrate on the surface of the test specimen, said displacement sensor detects and measures a linear displacement of said sensor shaft with respect to said penetrating pin for indicating the hardness of the test specimen.

35. The testing machine, as recited in claim 34, wherein said beam type load cell has two chambers defining a wall therebetween, and comprising two first strain gauges supported within said two chambers respectively and two second strain gauges supported at two sides of said wall to form said beam type load cell.

36. The testing machine, as recited in claim 35, wherein said Rockwell test device further has a pin receiving chamber for said sensor shaft movably disposed therein and comprises three transmission pins being placed between said guiding cylinder and a bottom of said sensor shaft and placed in a circular fashion, 120 degrees apart, across said bottom of said sensor shaft, such that when said slide device is driven to apply the force on said penetrating pin head for penetrating the surface of the test specimen, said guiding cylinder moves up and in turn, drives said three transmission pins and drives sensor shaft, so as to enable the linear displacement of said sensor shaft being detected and measured by said displacement sensor with respect to said penetrating pin.

37. The testing machine, as recited in claim 36, wherein an opening edge of said guiding cylinder has a flat surface for lying flush against the surface of the test specimen to ensure high accuracy in the displacement measurement.

38. The testing machine, as recited in claim 37, wherein said displacement sensor further comprises a wave spring and a spring supporter disposed therewithin for applying a force against said sensor shaft, and in turn, against said transmission pins, and in turn, against said guiding cylinder to provide resistance and to retain said guiding cylinder in a zero-displacement testing position when there is no specimen.

39. The testing machine, as recited in claim 38, wherein said displacement sensor further comprises two round steel leaves, which is fixed at an outer edge by said receiving chamber of a flange, wherein said two round steel leaves' inner holes are fixed at said sensor shaft to prevent said sensor shaft moving horizontally and to ensure only vertical movement.

40. The testing machine, as recited in claim 39, wherein said displacement sensor further comprises two fixed electrical terminals fixed within said pin receiving chamber, and one moveable electrical terminal fixed by said sensor shaft, wherein when said sensor shaft is displaced, said moveable electrical terminal moves between both fixed electrical terminals while said two fixed terminals and one moveable terminal form into two capacitances, wherein said two capacitances between said two fixed terminals and one moveable terminal vary as said sensor shaft moves, the difference of said two capacitances is proportional to the vertical displacement of said sensor shaft.

41. The testing machine, as recited in claim 40, wherein said displacement sensor further comprises one capacitance conditioner circuit which is located in said receiving chamber and converts a capacitance signal to an amplified analog signal.

42. The testing machine, as recited in claim 32, wherein said test device is a Vickers test device which comprises a Vickers penetrating pin for penetrating on the surface of the test specimen, and a connect interface contacting an interface on said slide device to communicatively link said Vickers test device with said control system, wherein said data processing circuit of said Vickers test device converts an analog signal of said force sensor into digital data to interface with said control system.

43. The testing machine, as recited in claim 42, wherein a full measurement range of said Vickers test device is 120 kg.

44. The testing machine, as recited in claim 32, wherein said test device is a Brinell test device which comprises a ball penetrating pin, and a connect interface contacting an interface on said slide device to communicatively link said Brinell test device with said control system, wherein said data processing circuit of said Brinell test device converts an analog signal of said force sensor into digital data to interface with said control system.

45. The testing machine, as recited in claim 44, wherein a full measurement range of the Brinell test device is up to 3000 Kg.

46. The testing machine, as recited in claim 32, wherein said test device is a microhardness test device which comprises a micro Vickers or Knoop penetrating pin, and a connect interface contacting an interface on said slide device to communicatively link said microhardness test device with said control system, wherein said data processing circuit of said microhardness test device converts an analog signal of said force sensor into digital data to interface with said control system.

47. The testing machine, as recited in claim 46, wherein a full measurement range of said Microhardness test device is 5 kg.

48. The testing machine, as recited in claim 32, wherein said test device is a tension-compression test device which comprises a thread hole for tension or compression measurement, and a connect interface contacting an interface on said slide device to communicatively link said tension-compression test device with said control system, wherein said data processing circuit of said tension-compression test device converts an analog signal of said force sensor into digital data to interface with said control system.

49. The testing machine, as recited in claim 48, wherein a full measurement range of the tension or compression test device 105 is up to 3000 Kg.

50. A method of testing a test specimen via a testing machine, comprising the steps of:
(a) selecting one of test devices in order to perform one of hardness test on the test specimen, wherein the hardness tests are selected from the group consisting of Rockwell hardness test, Vickers hardness test, Brinell hardness test, micro-hardness test, and tension-compression test;
(b) detachably coupling said test device at a slide device of a stand to perform the particular hardness test, wherein each of said test devices comprises its own force sensor and its own data processing circuit;
(c) controlling a force applied on the test specimen via a control system; and
(d) sending a digital data of said force sensor to interface with said control system.

51. The method, as recited in claim 50, further comprising a step of replacing another said test device to detachably couple with said slide device in order to perform another hardness test on said test specimen.

52. The method, as recited in claim 51, wherein the step (b) further comprises a step of contacting a connect interface of said respective test device with an interface on said slide device to communicatively link said test device with said control system.

53. The method, as recited in claim 52, wherein the step (d) further comprises a step of converting an analog signal of said force sensor into digital data to interface with said control system.

* * * * *